(12) United States Patent
O'Neill, III et al.

(10) Patent No.: US 9,861,449 B2
(45) Date of Patent: Jan. 9, 2018

(54) RADIOPAQUE MARKING IMPLEMENT

(71) Applicant: UNIVERSITY OF UTAH RESEARCH FOUNDATION, Salt Lake City, UT (US)

(72) Inventors: Kevin John O'Neill, III, Salt Lake City, UT (US); Joseph Passman, Ogden, UT (US); Ting Ruan, Taylorsville, UT (US); Andrea Tiede, Draper, UT (US); John Langell, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 284 days.

(21) Appl. No.: 14/671,584

(22) Filed: Mar. 27, 2015

(65) Prior Publication Data

US 2015/0272702 A1 Oct. 1, 2015

Related U.S. Application Data

(60) Provisional application No. 61/995,011, filed on Apr. 1, 2014.

(51) Int. Cl.
*H05G 1/28* (2006.01)
*A61B 90/00* (2016.01)

(52) U.S. Cl.
CPC ........ *A61B 90/39* (2016.02); *A61B 2090/395* (2016.02); *A61B 2090/3933* (2016.02); *A61B 2090/3966* (2016.02)

(58) Field of Classification Search
CPC ...... A61B 2090/3933; A61B 2090/395; A61B 2090/3966; A61B 90/39; C03C 8/16; C08F 20/44; C08F 214/08; C08F 214/18; C08K 3/22; C08K 3/24; C08K 3/30; C08K 3/34; C08K 3/36; C08L 2314/06; C08L 23/0815; A01N 25/00; A01N 25/02; A61K 8/19; A61K 31/155; A61K 8/20; A61K 8/23; A61K 8/39; A61K 8/731; A61K 8/86; A61K 2800/43; A61K 31/045; A61K 8/26; A61K 8/466; A61K 8/4946; A61K 9/08; A61Q 19/10; A61Q 19/02
USPC ........ 378/162, 163, 165, 210; 600/414, 431; 604/310; 424/401, 63, 64, 61
See application file for complete search history.

(56) References Cited

U.S. PATENT DOCUMENTS

| 4,813,062 | A | 3/1989 | Gilpatrick |
| 4,916,170 | A * | 4/1990 | Nambu ........... A61K 49/04 264/28 |
| 5,848,125 | A | 12/1998 | Arnett |
| 6,333,971 | B2 | 12/2001 | McCrory et al. |
| 6,419,680 | B1 * | 7/2002 | Cosman ........... G06T 3/4061 378/162 |

(Continued)

OTHER PUBLICATIONS

CDC. "Number of all-listed procedures from discharges from short-stay hospitals by procedure category and age: United States, 2009." 2009, pp. 1-2.

(Continued)

*Primary Examiner* — Irakli Kiknadze
(74) *Attorney, Agent, or Firm* — Michael Best & Friedrich LLP

(57) ABSTRACT

This disclosure provides marking implements for making radiopaque markings, and methods of using the same.

25 Claims, 21 Drawing Sheets

(56) References Cited

U.S. PATENT DOCUMENTS

| | | | |
|---|---|---|---|
| 6,972,022 B1* | 12/2005 | Griffin | A61B 90/39 604/112 |
| 8,152,401 B2* | 4/2012 | Sokoloff | B43K 1/12 401/198 |
| 8,320,993 B2 | 11/2012 | Sirimanne et al. | |
| 2002/0065461 A1* | 5/2002 | Cosman | G06T 7/73 600/426 |
| 2004/0127824 A1 | 7/2004 | Falahee | |
| 2007/0196453 A1* | 8/2007 | Zhang | A61K 9/7015 424/443 |
| 2008/0009718 A1 | 1/2008 | Zohman | |
| 2009/0253981 A1 | 10/2009 | Hamilton et al. | |
| 2011/0097134 A1 | 4/2011 | Allen et al. | |
| 2012/0046411 A1* | 2/2012 | Kulshrestha | A61L 29/04 524/528 |
| 2012/0150275 A1* | 6/2012 | Shaw-Klein | A61F 2/88 623/1.15 |
| 2012/0263767 A1* | 10/2012 | Oudry | A61Q 1/06 424/401 |
| 2012/0302863 A1* | 11/2012 | O'Neill | A61B 19/54 600/407 |

OTHER PUBLICATIONS

Pisani L, Lockman D, Jaffray D, Yan D, Martinez A, Wong J. "Setup error in radiotherapy: online correction using electronic kilovoltage and megavoltage radiographs." International Journal of Radiation Oncology Biology Physics. 2000;47:825-839.

Rathod S, Munshi A, Agarwal J. "Skin markings methods and guidelines: A reality in image guidance radiotherapy era." South Asian Journal of Cancer. 2012;1:27-29.

Probst H, Dodwell D, Gray JC, Holmes M. "An evaluation of the accuracy of semi-permanent skin marks for breast cancer irradiation." Radiography. 2006;12:186-188.

Cuzner B, Klepak P. "Antiperspirants and deodorants." In: Butler H, editor. Poucher's Perfumes, Cosmetics and Soaps: Springer Netherlands; 1993. p. 3-26.

FDA "Summary of Color Additives for Use in the United States in Foods, Drugs, Cosmetics, and Medical Devices." Available online as early as 2009. http://www.fda.gov/forindustry/coloradditives/coloradditiveinventories/ucm115641.htm.

Bic Corporation. "Round Stic." http://www.bicworld.com/us/products/details/12/round-stic; 2014.

Viscot Medical L. "Sterile Mini Reg/Fine Tip Traditional Ink Marker w/ Ruler" #1451SR-100. http://www.viscot.com/1451SR-100?tag=1451SR-100; 2014.

FDA "Guidance for Industry: Topical dermatological drug product NDAs and ANDAs—In vivo bioavailability, bioequivalence, in vitro release, and associated studies." 1998. 1-19.

Mathieu KB, Kappadath SC, White RA, Atkinson EN, Cody DD. "An empirical model of diagnostic x-ray attenuation under narrow-beam geometry." Medical Physics. 2011;38:4546-4555.

Space OAR, "TraceIT Hydrogel" available online as early as 2013, http://www.augmenix.com/products/traceit/.

"Radiopaque™ Medical Inks—Developed for Medical / Diagnostic Applications" CI Medical Imprinting Technology, avalable online as early as 2007, http://www.cimedical.com/Inks/radiopaque-ink.html.

Bard Biobsy, "Breast Tissue Markers," available online as early as 2009, http://www.bardbiopsy.com/products/index_markers.php.

Radiopaque Solutions, Inc., home webpage, available as early as 2013, http://www.radiopaquel.com/home.html.

Terumo Interventional Systems, "Pinnacle® Destination® Guiding Sheath" available as early as 2015, http://www.terumois.com/products/sheaths/destination.aspx.

Carbofix Orthopedics, home page, available as early as 2011, http://www.carbo-fix.com/Products/CarboFixNails/Radiopaquemarkers.aspx.

Universal Medical, home page, available as early as 2015, http://www.universalmedicalinc.com/Lead-Markers-s/314.htm.

IZI Medical Products, home page, available as early as 2000, http://www.izimed.com/whats_new.shtml.

Suremark, home page, available as early as 2010, http://www.suremark.com/catalog/.

* cited by examiner

RADIOPAQUE MARKING IMPLEMENT

CROSS-REFERENCE TO RELATED APPLICATIONS

This application claims priority to U.S. Provisional Patent Application No. 61/995,011, filed Apr. 1, 2014, which is incorporated herein by reference in its entirety.

BACKGROUND

Radiography and fluoroscopy are imaging techniques that use electromagnetic radiation other than visible light, namely x-rays, to view the internal structure of a non-uniformly composed and opaque object (i.e., a non-transparent object of varying density and composition), such as the human body. To create an image of the object, a heterogenous beam of X-rays is produced by an X-ray generator and is projected toward the object. A certain amount of X-ray is absorbed by the object, which is dependent on the particular density, composition and thickness of that object. The X-rays that pass through the object are captured behind the object by a detector, and are thus used to generate images of the object's internal structures. As many as 20 million radiological and fluoroscopic imaging procedures are performed on humans each year.

Many radiological and fluoroscopic imaging procedures require marking the object with a radiopaque material that inhibits or prevents x-rays from passing through the material. For example, radiopaque materials may be used during fluoroscopic procedures to mark proper incision sites. Marking a patient's skin with a radiopaque material may help inhibiting systematic setup error in standard radiological procedures, and may improve the accuracy of treatment.

Existing devices for marking a patient's skin during radiological procedures include stickers with metal BBs, radiopaque tape, metallic tattoos, and marking pens. Each of these devices has its drawbacks. There is a thus a need to develop a flexible, cheap, and painless method for surgeons, radiologists, and technicians to mark patient skin with radiopaque material during diagnostic, therapeutic, and surgical procedures.

SUMMARY

This disclosure provides marking implements for making radiopaque markings, and methods of making and using the same.

In some embodiments, the marking implements comprise a marking element formed of a composition comprising a carrier and a plurality of bismuth trioxide particles dispersed in the carrier. The composition is a thixotropic solid that maintains its shape at ambient temperatures but is deposited on skin at thicknesses between about 0.1 mm and about 1.5 mm when a shear force of between about 10N to about 35N is applied between the composition and the skin. The composition has an attenuation coefficient of greater than about 1,000 Hounsfield units (HU) at a thickness of about 0.6 mm for an x-ray having an incident intensity of about 135 kVp and about 1.5 mA.

In some embodiments, the marking implements comprise a marking element formed of a composition comprising a carrier and a plurality of bismuth trioxide particles dispersed in the carrier, the carrier comprising about 35 wt % to about 50 wt % propylene glycol, about 10 wt % to about 15 wt % dipropylene glycol, and about 2 wt % to about 15 wt % sodium stearate.

The marking implements of the present disclosure may be used for a variety of applications, including, but not limited to, surgical procedures. For example, the marking elements may be used in methods for facilitating surgical procedures, comprising locating a position on the skin of a patient relative to a target surgical site, marking the position on the skin using the marking implement, and subjecting the target surgical site and the marked location to x-ray exposure to view the target surgical site and the mark under x-ray.

Other aspects of the marking implements and methods of making and using the same will be understood with reference to the drawings, the detailed description and the claims.

DETAILED DESCRIPTION

This disclosure is not limited in its application to the details of construction and the arrangement of components set forth in the following description. The disclosure may provide other embodiments and may be practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

It should be understood that, as used herein, the term "about" is synonymous with the term "approximately." Illustratively, the use of the term "about" indicates that a value includes values slightly outside the cited values. Variation may be due to conditions such as experimental error, manufacturing tolerances, variations in equilibrium conditions, and the like. In some embodiments, the term "about" includes the cited value plus or minus 10%. In all cases, where the term "about" has been used to describe a value, it should be appreciated that this disclosure also supports the exact value.

This disclosure provides radiopaque marking implements, and methods of making and using the same. The marking implements may comprise a marking element formed of a composition comprising a carrier and radiopaque particles, such as bismuth trioxide particles, dispersed in the carrier. The marking implements further may comprise a body for supporting and storing the marking element.

Figure 1:
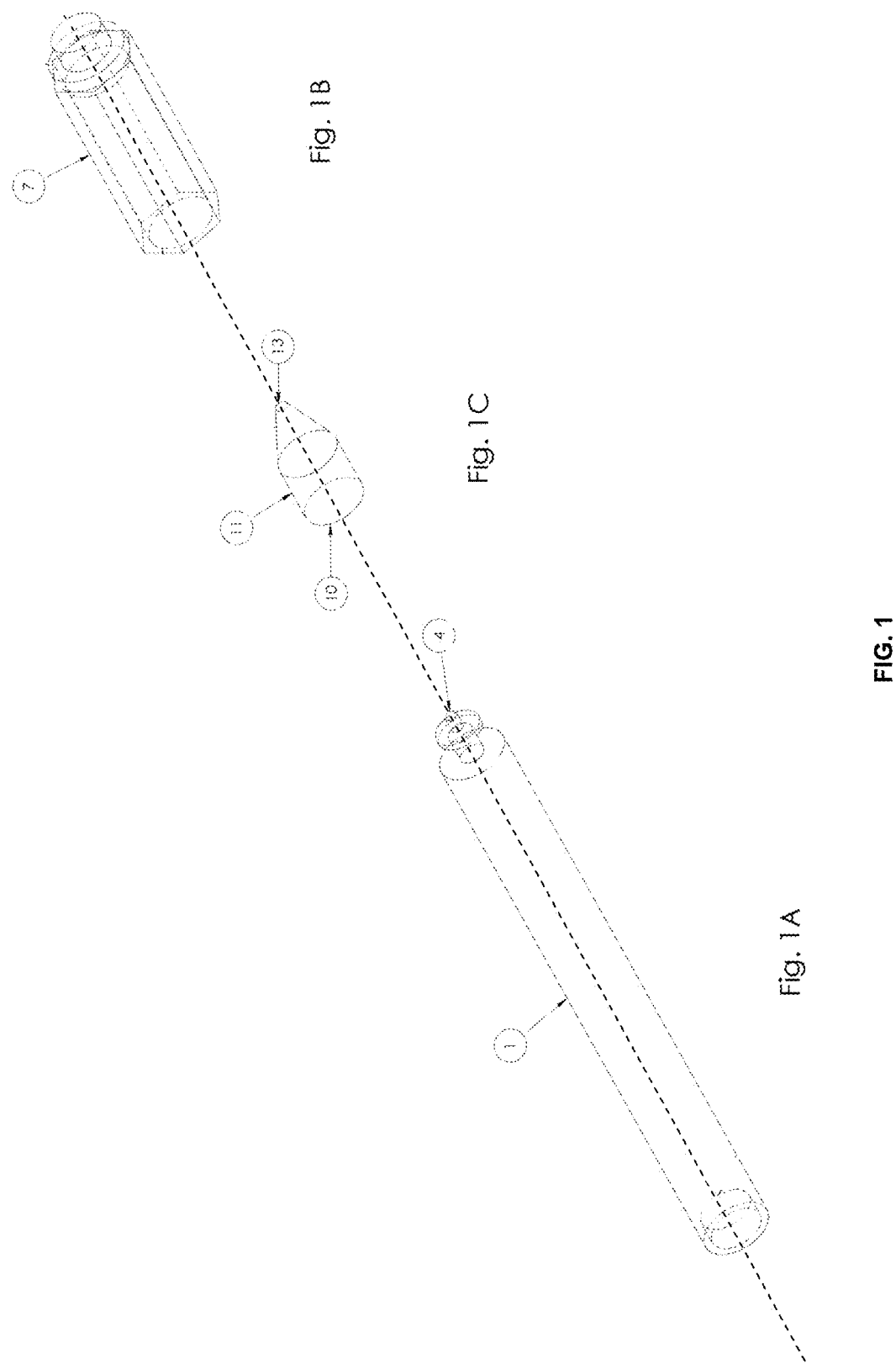
FIG. 1 is an exploded view of a marking implement according to embodiments of the present disclosure.

FIG. 1 shows an exemplary embodiment of a marking implement according to aspects of the present disclosure. The marking implement may include a body 1, a marking element 11, and an optional storage cap 7.

The body 1 may include any structure adapted to support and/or store the marking element 11. For example, the body may be generally elongate to provide an object that can be held by a user while applying the marking element to an object, such as a patient. The body may be formed of any material, and may have any shape consistent with its function. For example, the body may be formed of high density polyethylene, and may be substantially cylindrical, although any shape may be used (e.g., hexagonal, square, etc.). The body may include one or more structures for engaging and/or supporting the marking element. For example, the body may include a support structure 4 on which the marking element may be formed (e.g., via a casting process) that functions to retain the marking element on the end of the body, and to support the marking element to provide additional strength during use. In some embodiments, the support structure may be adapted to retract into and extend from the main body of the marking implement for storage of the marking element. Some marking elements may include a storage cap 7 for protecting the marking element from unintended engagement with other objects.

The marking element 11 may be attached or otherwise engaged with the end of the body 1. In some embodiments, the marking element may be casted in a mold to form a structure having a shape and size that makes it ideal for individual uses as a marker. The marking element may include an interfacial region 10 for engaging the main portion of the pen body, and a tip 13 for providing a precise mark on a desired object.

The marking element may be formed of any material that allows for both visual and radiographic marking of patients and objects for use on all areas where flexible radiopaque and visible marking is beneficial. The marking element may comprise a non-toxic composition that can easily be applied in a thin, even and consistent layer, and that includes a radiopaque substance. More specifically, the marking element may be formed of a composition comprising a carrier, a plurality of radiopaque particles, and optionally a colorant. The composition may be a thixotropic solid that maintains its shape at ambient temperatures but is deposited on skin at thicknesses between about 0.1 mm and about 1.5 mm when a shear force of between about 10N to about 35N is applied between the composition and the skin, and that has an attenuation coefficient of greater than about 1,000 Hounsfield units (HU) at a thickness of about 0.6 mm for an x-ray having an incident intensity of about 135kVp and about 1.5 mAs The carrier may comprise a mixture of one or more compounds that provide the base material for the thixotropic solid. For example, the carrier may comprise one or more of propylene glycol, dipropylene glycol, polyethylene glycol, sodium stearate, collagen, sorbitol, fumed silica, cyclomethicone, silicon, and talc, among others. In some embodiments, the carrier may comprise about 35 wt % to about 50 wt % propylene glycol, about 10 wt % to about 15 wt % dipropylene glycol, and about 2 wt % to about 15 wt % sodium stearate. In some embodiments, the carrier further may comprise about 10 wt % to about 15 wt % fumed silica. In some embodiments, the carrier may comprise between about 5 wt % and about 10 wt % cyclomethicone.

The radiopaque particles may be made from virtually any metal, preferably biocompatible metals, including, but not limited to, bismuth trioxide, bismuth tungsten oxide, barium sulfate, bismuth (III) titanate, bismuth telluride, bismuth molybdate, gold, gadolinium, silver, titanium, and tungsten, among others. In preferred embodiments, the radiopaque particles may be bismuth trioxide. The radiopaque particles may be dispersed in the carrier after the carrier has been heated to form a liquid. The concentration of the particles in the liquid mixture may be between about 50 g/L and about 750 g/L, such as between about 100 g/L and about 600 g/L, or between about 300 g/L and about 550 g/L. The liquid mixture then may be casted onto the body of a marking implement by pouring the mixture into a mold (e.g., a silicon mold) and allowing it to cool, thereby forming a solid. The radiopaque particles may have average diameters between about 90 nm and about 210 nm, which is large enough to inhibit the likelihood the particles can enter the pores of skin and cause a subcutaneous granuloma, while small enough to inhibit precipitation of the particles during the casting process. Surprisingly, it has been observed that bismuth trioxide attenuates at substantially higher attenuation coefficients than were theoretically predicted using the Beer-Lambert Law. For example, marking elements having bismuth trioxide concentrations of about 500 g/L, when applied at a thickness of about 0.6 mm, were surprisingly found to have attenuation coefficients greater than about 2,000 HU, such as greater than about 3,000 HU, for an X-ray having an incident intensity of about 135 kVp and about 1.5 mAs. This unexpected finding allows for the use of lower concentrations of radiopaque metals and/or application of thinner layers during a procedure.

In some embodiments, the marking element may comprise a coloring agent (e.g., a pigment or dye) to provide visual contrast with the color of the object to which it is being applied (e.g., human skin). For example, the marking element may comprise erioglaucine disodium salt, which has been observed to contrast well with a wide variety of skin colors.

The marking element may be readily washable in water, so as not to be visible to the naked eye. This is important, so that incorrectly placed marks do not radiographically confound the subsequent correct placement of a mark.

The marking implement of the present disclosure may be used for a wide variety of applications, including medical diagnosis, radiotherapy, surgery, and standard radiographic procedures. For example, the marking implements of this disclosure may be used in methods for facilitating a surgical procedure, comprising locating a position on the skin of a patient relative to a target surgical site, marking the position on the skin using the marking implement, and subjecting the target surgical site and the marked location to x-ray exposure to view the target surgical site and the mark under x-ray.

EXAMPLES

The following examples disclose various embodiments of marking implements. Comparative examples I and II show attempts to produce effective marking implements that failed to yield satisfactory results, whereas Example 3 shows a marking element that permitted deposition of a thin even layer onto skin, while still providing for adequate attenuation of x-rays. The following examples are presented solely to illustrate the present invention, and to assist one of ordinary skill in making and using the same. The examples are not intended in any way to otherwise limit the scope of the invention.

Comparative Example I—Liquid Ink Marking Implement

Figure 2:
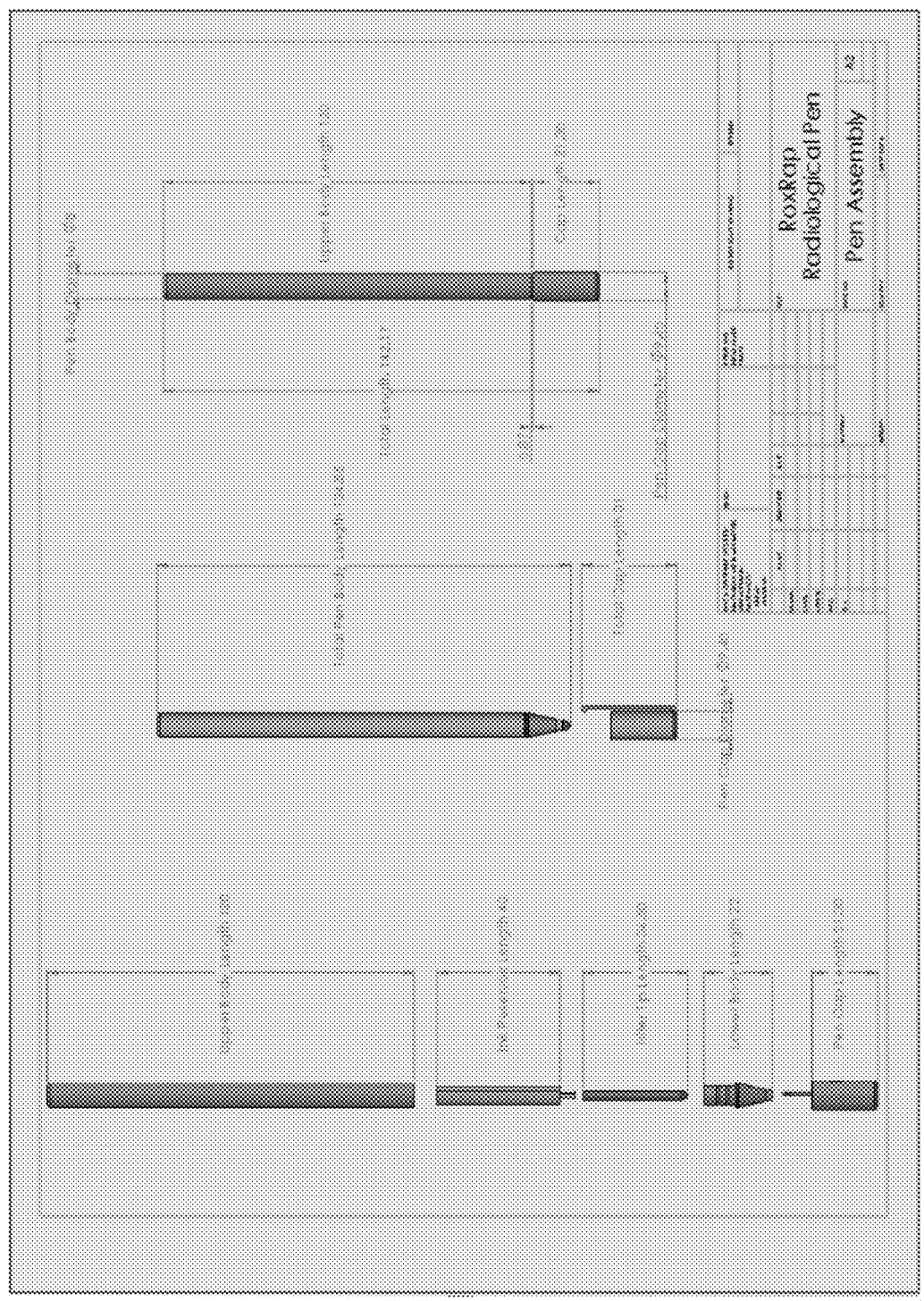
FIG. 2 is an assembly drawing showing a marking implement with a liquid making composition.

A model of a liquid ink marking implement was generated. As shown in FIG. 2, the marking implement consisted of liquid ink, an ink reservoir, a filter tip, and a high density polyethylene pen bodies. Components were scavenged from other pens to make a simple prototype pen, shown in FIG. 3. We used the pen body/casing from a BIC Round Stic ball-point pen, and the marker nib and reservoir from a Viscot surgical marker 1451. The reservoir and pen nib were cleaned by flowing water from a sink. After cleaning and drying, the pen nib and reservoir were allowed to soak in blue food coloring purchased from Smith's, a local grocery store. The pen body was spray painted with a blue and yellow coloring scheme. The pen nib and reservoir were then placed inside the pen body. The pen was used to write on printer paper and skin. This was purely a proof of concept on manufacturing a marker.

Figure 3:
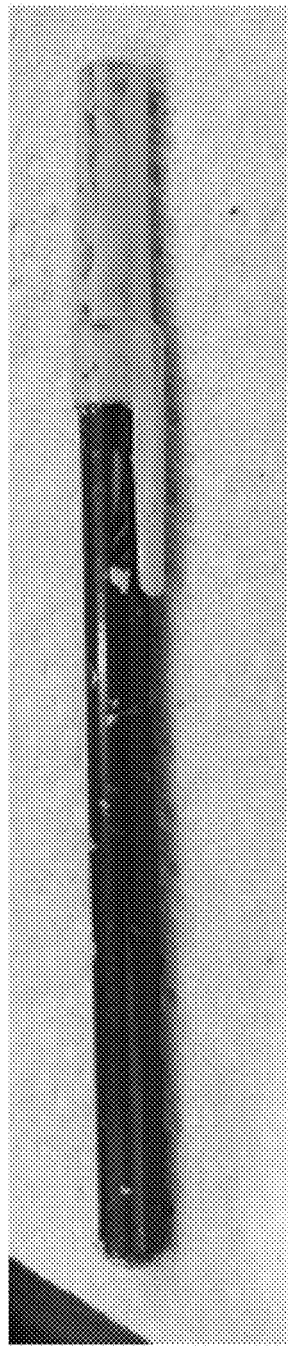
FIG. 3 is a photograph of a prototype of a marking implement with a liquid marking composition.
Figure 4:
FIG. 4 is a photograph showing application of the liquid marking composition from the marking implement of FIG. 3 to human skin.

As shown in FIG. 3, the construction was extremely messy, and as shown in FIG. 4, the marking on skin was blotchy and erratic.

Comparative Example II—Gel Ink Marking Implement

We had hopes of better suspending bismuth trioxide nanoparticles to improve the homogeneity of the radiopaque compound on human skin. The gel continuous phase was composed of food-grade gelatin and water. We used a toothpaste tube with a modified high density polyethylene end-piece to dispense the gelatinous phase. The gelatinous ink marked erratically on human skin.

Figure 5:
FIG. 5 is a photograph of a prototype of a marking implement with a gelatinous marking composition.

The gel-ink casing and dispersal mechanism shown in FIG. 5 was fabricated by emptying a crest "Travel Tube" toothpaste canister, and custom-machining a high density polyethylene cap in a curvilinear shape to fit the opening of the toothpaste tube.

Gelatinous ink was made by dissolving Knox brand food-grade collagen gel (at a concentration of 29.6 g/L) in boiling water, allowing the collagen/water mixture to cool to 60° C., and then adding erioglaucine disodium salt (at a concentration of 40 g/L) to the mixture.

Figure 6:
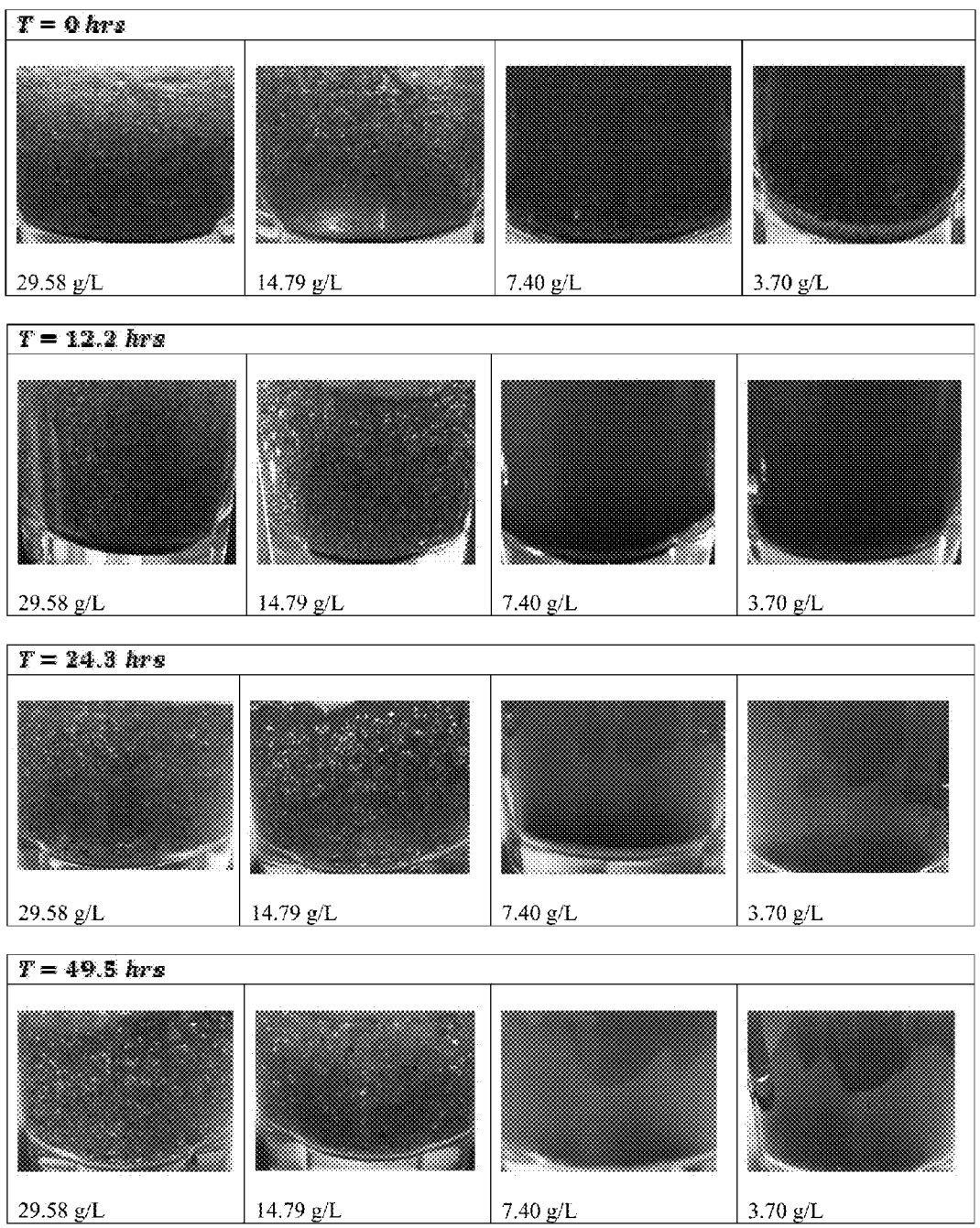
FIG. 6 is a series of photographs showing gelatinous marking compositions having varying concentrations of pepper flakes at varying points of time.

To observe time-dependent sedimentation, food grade pepper flakes were added to the gelatinous ink at concentrations of 3.70 g/L, 7.40 g/L, 14.79 g/L and 29.58 g/L. As shown in FIG. 6, no qualitative sedimentation occurs over 49.5 hours at the higher concentrations of pepper. This showed that the gel ink formulation helped to stabilize heavy particles.

Figure 7:
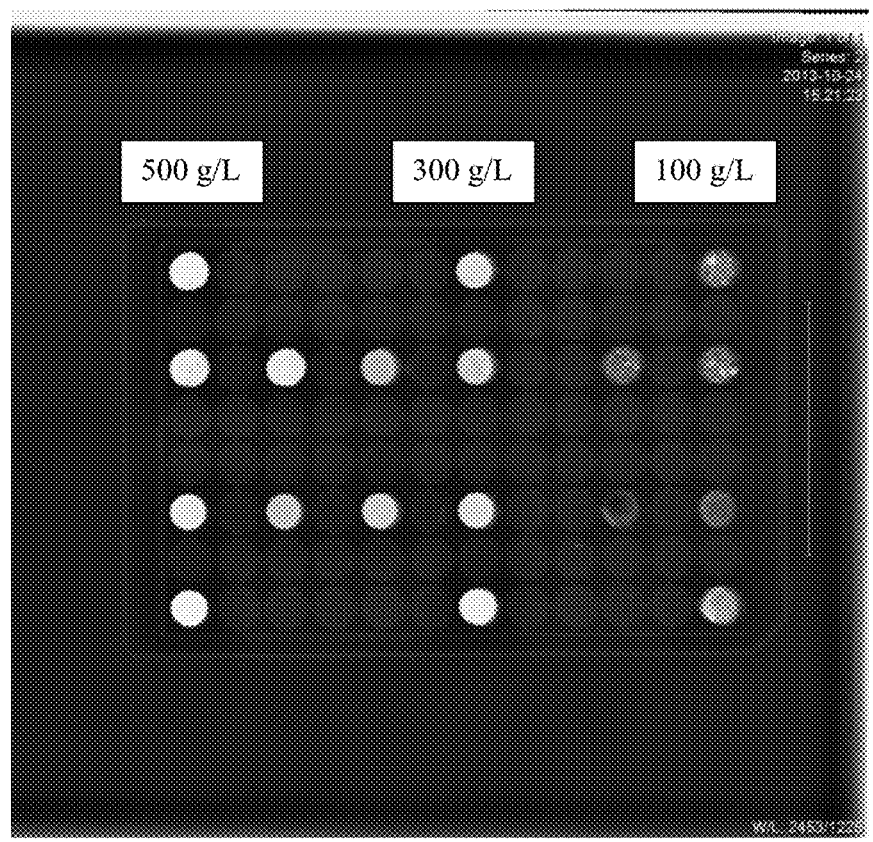
FIG. 7 is a CT scan of a 96 well plate with wells containing various gelatinous marking compositions having various concentrations of bismuth trioxide.

Bismuth trioxide was added to the gelatinous ink at concentrations of 100 g/L, 300 g/L, and 500 g/L. As shown in FIG. 7, a 96 well plate was prepared with the three concentrations of bismuth trioxide, and the attenuation for the samples was characterized under CT "bone" and "soft tissue" settings. A trained CT technician ran the tests and we used proprietary Siemens software to obtain the HU attenuation values.

Figure 8:
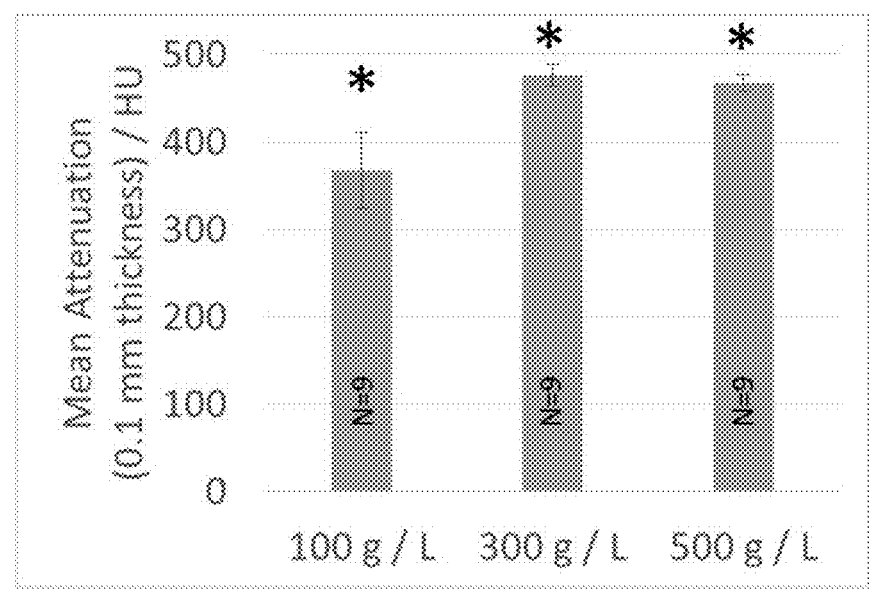
FIG. 8 is a bar chart showing mean attenuation at 0.1 mm thickness of gelatinous marking compositions having varying concentrations of bismuth trioxide.

As shown in FIG. 8, the gel ink containing 100, 300 and 500 g/L bismuth trioxide, when applied at thicknesses of about 0.1 mm, attenuated at approximately 300-500 HU under CT radiation.

Figure 9:
FIG. 9 is a photograph of a gelatinous marking composition applied to human skin.

As shown in FIG. 9, the gel ink spread extremely erratically on skin. Moreover, the gel was too thick, and required more than 30 N of force to be extruded from the gel tube. Finally, the gel ink hardened with storage time, making it increasingly difficult to remove from the tube. Although attenuation was good, the gel ink composition failed due to the inability to easily deposit even layers, and to store over time.

Comparative Example III—Thixotropic Solid Marking Implement

Figure 10:
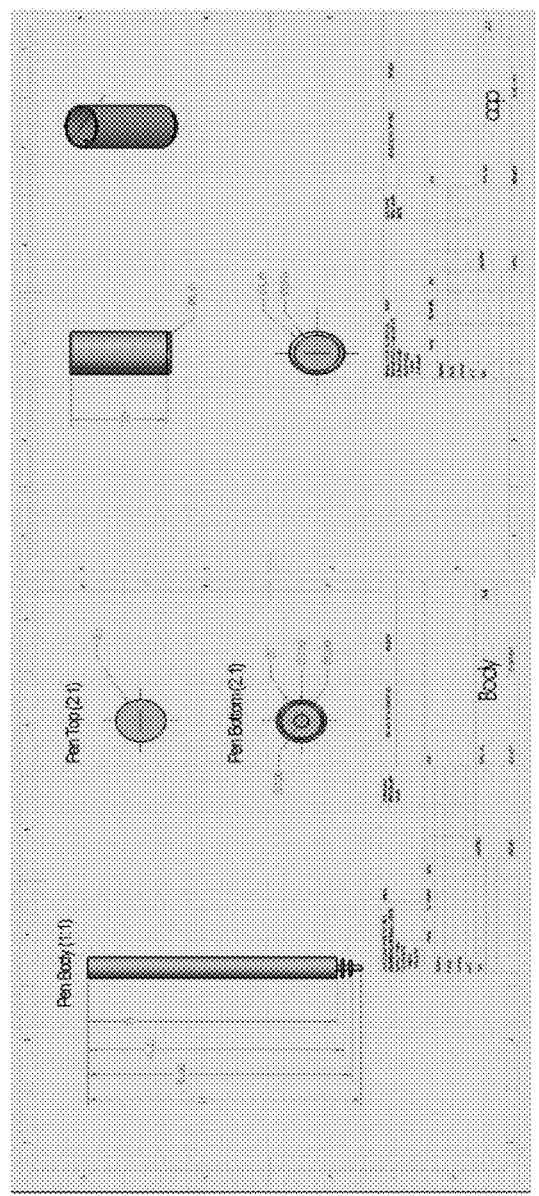
FIG. 10 is an assembly drawing showing a marking implement for use with thixotropic solid marking compositions.

The 3$^{rd}$ version of the marking implement consisted of a solid pen body with two fins and a cap, as shown in FIG. 10. A marking element comprising a homogenous thixotropic composition was attached to the fins. The composition can be applied easily/smoothly to the skin, and can be washed with water or wiped off non-abrasively with alcohol wipes.

Figure 11:
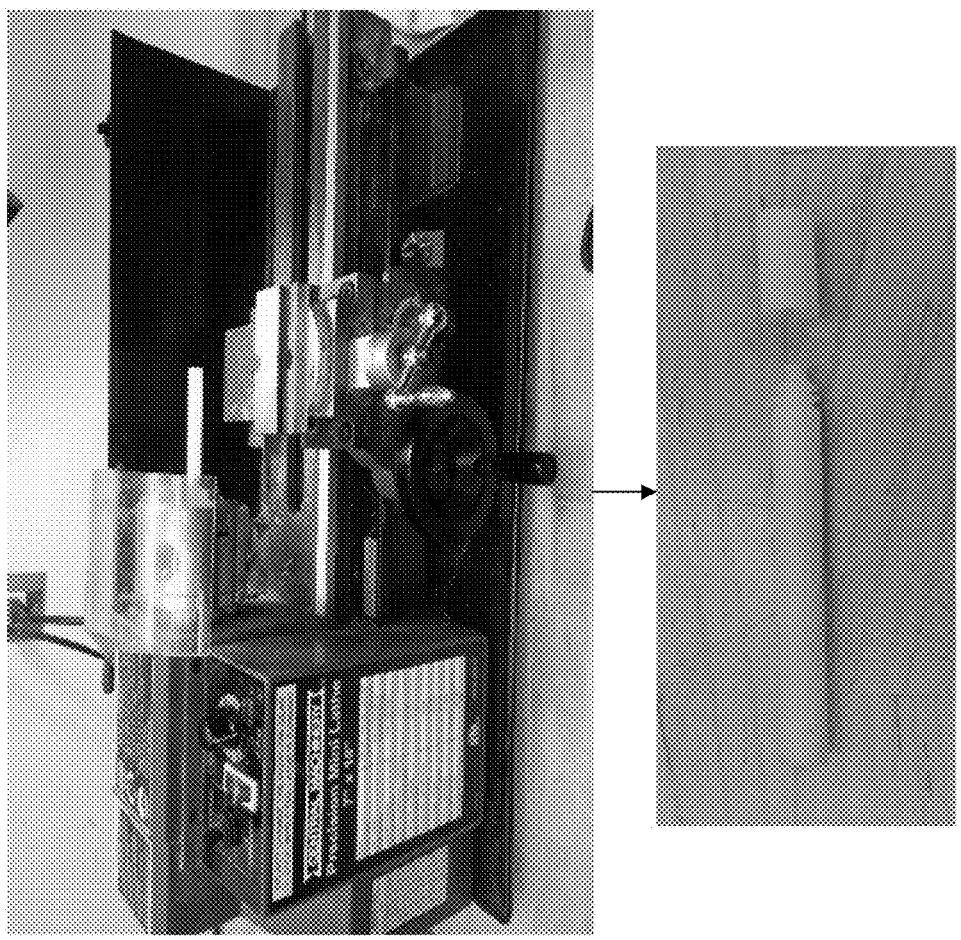
FIG. 11 is a pair of photographs depicting lathe manufacturing of a body and cap from 10 mm diameter high density polyethylene rod.

As shown in FIG. 11, the body and cap of the marking implement were made from 10 mm diameter rod high density polyethylene on a mini-lathe.

Figure 12:
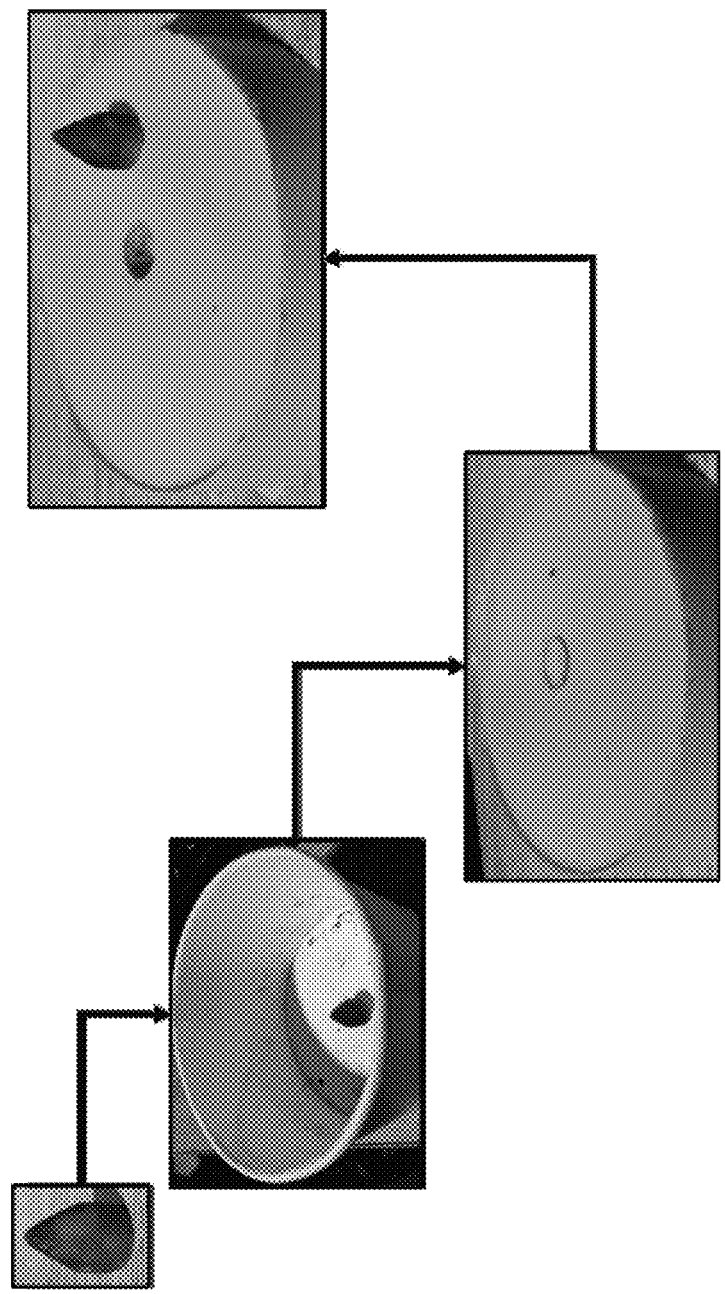
FIG. 12 is a diagram showing methods for casting thixotropic solid marking compositions.
Figure 13:
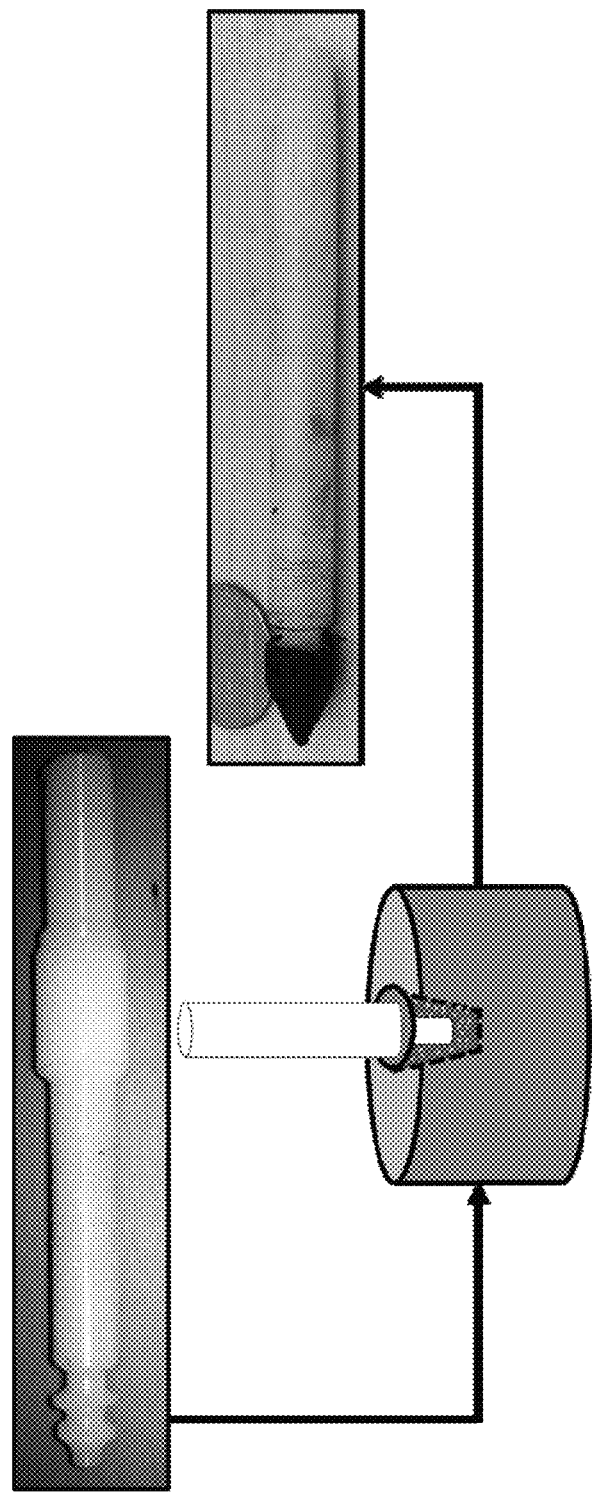
FIG. 13 is a diagram showing methods for forming marking implements comprising thixotropic solid marking compositions.

The marking element was formed as follows. First, Arm & Hammer Ultra Max deodorant was heated to 70° C., until melted. Erioglaucine disodium salt was added to a concentration of 40 g/L. Bismuth trioxide was added to concentrations of 100 g/L, 300 g/L and 500 g/L, and stirred under heat at 70° C. The liquid mixtures were then casted into marking elements using a silicon mold, as shown in FIGS. 12 and 13.

Figure 14:
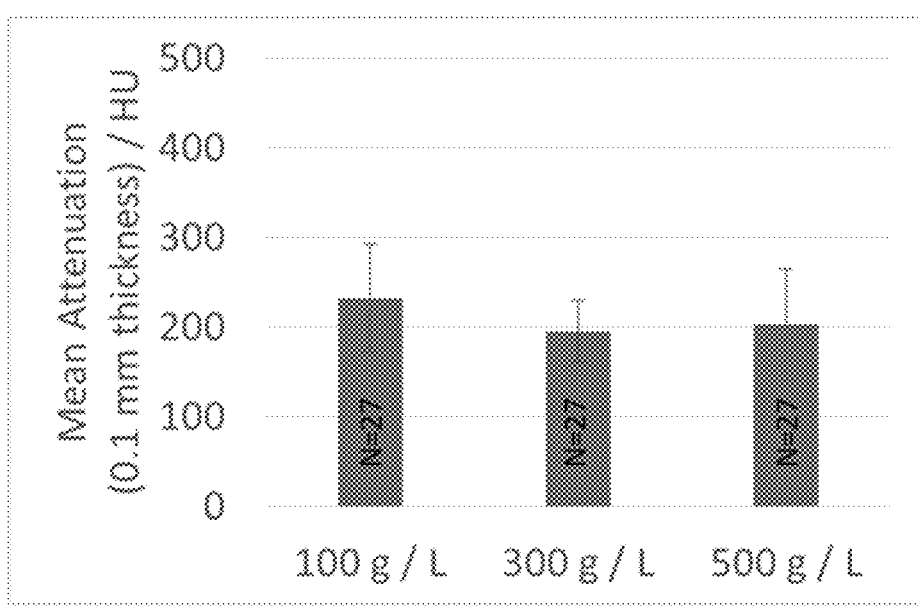
FIG. 14 is a bar chart showing mean attenuation at 0.1 mm thickness of thixotropic marking compositions having varying concentrations of bismuth trioxide.
Figure 15:
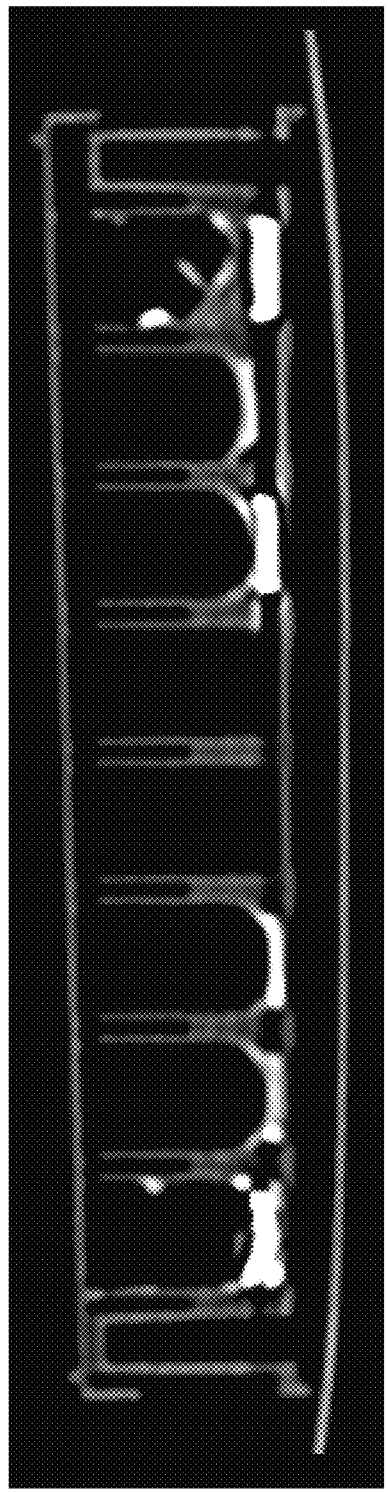
FIG. 15 is a CT scan showing that the thixotropic marking compositions of this disclosure have homogenous radiopacity.

The attenuation under CT "bone" and "soft tissue" settings was characterized, as shown in FIG. 14. Moreover, the semi-solid ink samples showed good homogeneity under CT radiation, as shown in FIG. 15.

Dynamic light scattering was used to determine the time-dependent agglomeration of our nanoparticle dispersion. We chose to use dynamic light scattering (DLS) to characterize the change in polydispersity index (ΔPDI) at time points of 1 and 4 weeks after production. to verify that the dispersion was not changing dispersity over a 4 week period. The following formula was used to calculate ΔPDI:

$$\Delta PDI = \left(\frac{\sigma[4 \text{ weeks aging}]}{D[4 \text{ weeks aging}]}\right)^2 - \left(\frac{\sigma[1 \text{ week aging}]}{D[1 \text{ week aging}]}\right)^2$$

where σ is the standard deviation of the particle size distribution and D is the mean particle diameter.

Because the polydispersity index takes into consideration both the standard deviation and mean particle diameter, we chose to characterize the particle size for a complete analysis of agglomeration states. We pipetted solutions of 100, 300, and 500 g/L bismuth (III) oxide nanoparticles into bulk flasks. We diluted each flask with DI water to 10% of its original concentration. This dilution step was necessary to obtain a sufficient light scattering signal.

Figure 16:
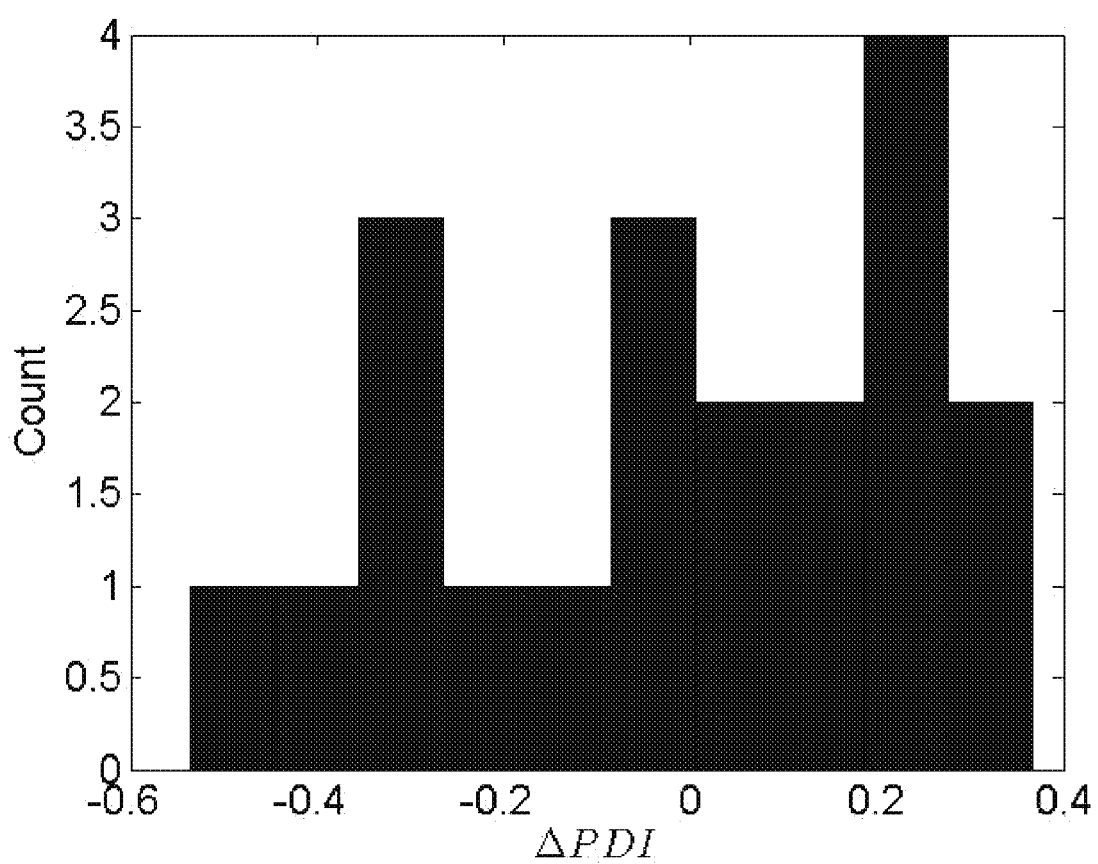
FIG. 16 is a bar chart showing the change in polydispersity index over a 4 week period for the thixotropic marking compositions of this disclosure, indicating that the width of the particle size distribution does not vary much over the four week period, thus supporting the conclusion that the bismuth trioxide is not agglomerating.

As shown in FIG. 16, the standard deviation difference between the two different time points is relatively small in comparison to the particle size. This data supports the conclusion that the distributions do not significantly broaden over a four week period. The change in polydispersity index does not indicate a significant change in agglomeration state.

Figure 17:
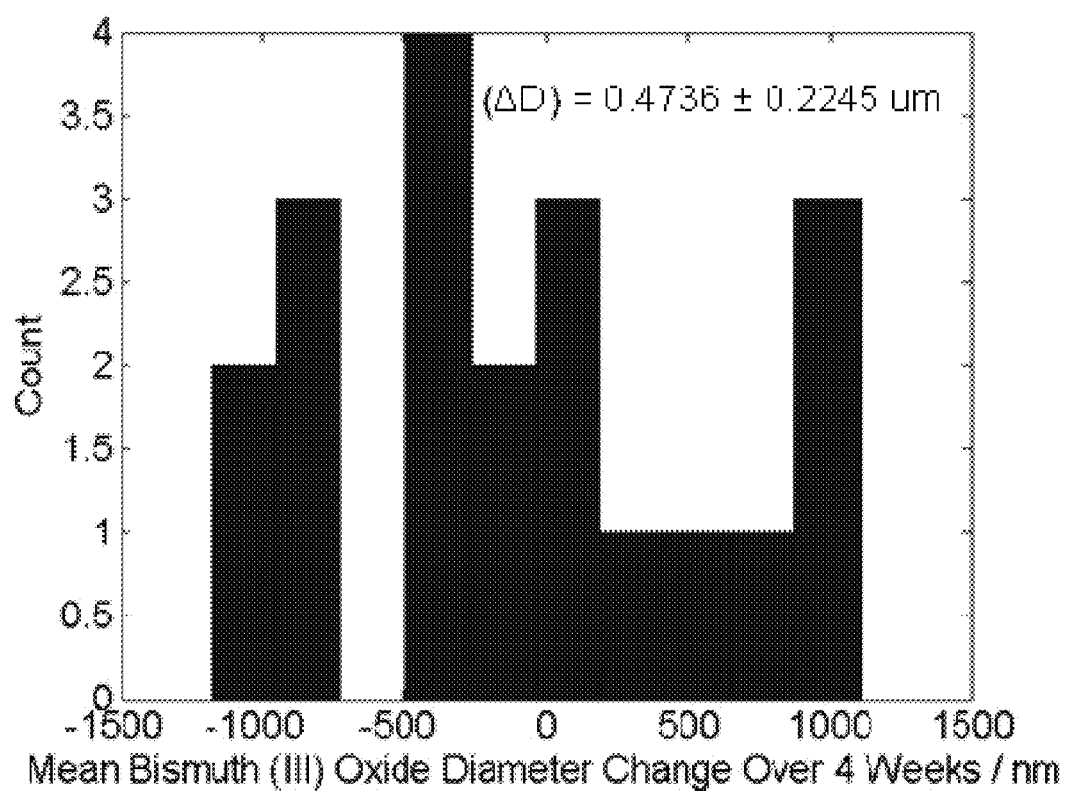
FIG. 17 is a bar chart showing the mean particle size of bismuth trioxide over a 4 week period for the thixotropic marking compositions of this disclosure.

As shown in FIG. 17, the change in mean particle size (ΔD) over a 4 week period is 0.4736±0.2245 um. The change in mean particle size was used to ensure that it was sufficiently small. This ensures that the standard deviation of the particle size distribution was the dominating factor in the calculation of polydispersity index. By ensuring that the change in particle size was approximately less than 500 nanometers, we were able to confidently assess that the standard deviation of the particle distribution was the dominating factor in the change in polydispersity index. Furthermore, we could conclude that the nanoparticles successfully avoided agglomeration over a time period of four weeks.

A slough rate test was conducted on paper to determine how much of the marking element composition comes off of the pen during a standard writing stroke. The thixotropic composition had a slough rate of 0.093±0.012 cm$^3$/min. This value is a low approximation for the slough rate on skin, because would be warmer than the paper test patches, leading to more sloughed material. Also, human skin is deformable and plastic, allowing the skin to grab at the thixotropic solid.

An evaporation test was conducted to assess how much moisture is lost during storage, to provide a sense of shelf life. The evaporation rate was approximately −1.35±1.1% weight/week over a 5 week period in the dry climate of Utah. We determined this to be an acceptable loss for a 3 month projected shelf life.

The pen tip must remain structurally sound after experiencing 50 cycles of 20N loading. A pen tip that was salvaged from a Viscot surgical marking pen was placed into an Instron for a cyclic compression test. The pen tip was angled 75° from the horizontal axis in order to simulate a writing angle. The Inston would load the pen for 50 cycles. Each cycle maxing out at 20N. The solid pen did not break off, instead it deformed with the increase in force. This means that the solid ink prototype will remain secure at more normal writing forces of <10N.

Figure 18:
FIG. 18 is a photograph showing of the thixotropic solid of this disclosure applied to human skin.

A score of 4.8±0.2 out of 5 was obtained on a user survey asking if the semi-solid ink was visible to the eye when applied to human skin. We passed the test and received verbal comments such as "very easily visible." Furthermore, the users said the ink applied smoothly and cleanly to human skin, as shown in FIG. 18.

The thixotropic composition had a pH=8.2489±0.1594, which falls within accepted values of pH=7-8.5 for non-irritating hand soaps.

The resilience of the semi-sold ink pen tip was tested under simulated writing conditions such that the ink tip would show less than 25% deformation under 20N compressive force. A pen tip that was salvaged from a Viscot surgical marking pen was placed into an Instron for a cyclic compression test. The pen tip was angled 75° from the horizontal axis in order to simulate a writing angle. The Inston would load the pen for 50 cycles. Each cycle maxing out at 20N. The pen tip experienced a total of 10.5±1.5% deformation from its original state. This deformation measure was acquired from the extension data of the Instron. The further the Instron had to extend to reach 20N, the more deformed the pen tip had become. This 10.5±1.5% deformation is an inflated measure as the Instron compromised the structure of the pen tip when the pen tip was clamped into the Instron. Both this structural change, and the edge effects of the clamp, would cause the deformation measurement to be higher than what it would be in actual use.

Calculations were conducted to predict how different concentrations of bismuth trioxide would attenuate radiation at various applied layer thicknesses, both as a predictive guide for future development, and for comparison of various radiopaque contrast agents. The Beer-Lambert Law can be used to describe the attenuation of a monochromatic x-ray beam under simple adsorption. The Beer-Lambert Law does not account for inelastic or elastic scattering and/or x-ray generation due to beam-material interactions. X-ray adsorption is a stochastic process, occurring when an incident beam induces an electronic transition in the probed substrate. Complex models of the attenuation process use Monte Carlo simulation and parameterized coefficients to modify the Beer-Lambert Law, accounting for elastic and inelastic scattering and polychromatic x-ray source. The simple Beer-Lambert equation, shown below, was used as a model to predict the attenuation coefficient of bismuth trioxide at various applied layer thicknesses.

$$I(x;E) = I_0(E)e^{\mu_m(E)x_m}$$

where $I(x;E)$ is the distance-dependent attenuated intensity calculated at a fixed energy, $I_0(E)$ is the incident intensity of the x-ray beam at a fixed monochromatic energy, $\mu_m$ is the multicomponent mass adsorption coefficient, and $x_m$ is the mass thickness.

The multicomponent mass adsorption coefficient is calculated as a percent mass-weighted sum of the single component mass adsorption coefficient.

$$\mu_m = w_1\mu_{m,1} + w_2\mu_{m,2} + \ldots = \Sigma w_i\mu_{m,i}$$

A database of atomic mass attenuation coefficients for elements Z=1-92, maintained by NIST was used to calculate the multicomponent mass attenuation coefficients.

The mass thickness of the material is calculated as a function the density (g/cm$^3$) of a homogeneously suspending nanoparticle solution. The volume is imagined to be a box and is scaled by a 1 cm side length to get the mass thickness.

$$x_m = \rho \cdot 1 \text{ cm}^2$$

A distance-dependent mass adsorption coefficient was back-calculated from the distance-dependent attenuated intensity (calculated at a fixed energy), $$\mu_m(x; E) = \frac{\log\left(\frac{I(x;E)}{I_0(X)}\right)}{\mu_m(E)}$$

We converted the mass attenuation coefficient to the linear attenuation coefficient by multiplying the distance-dependent attenuation coefficient at fixed energy by the material density.

$$\mu(x;E) = \mu_m(x;E) \cdot \rho$$

We solved for the distance-dependent HU value at a fixed energy as the relative error from the linear attenuation coefficient of water.

$$HU(x; E) = \left(\frac{\mu(x;E) - \mu_{H2O}(E)}{\mu_{H2O}(E)}\right) * 1000$$

Figure 19:
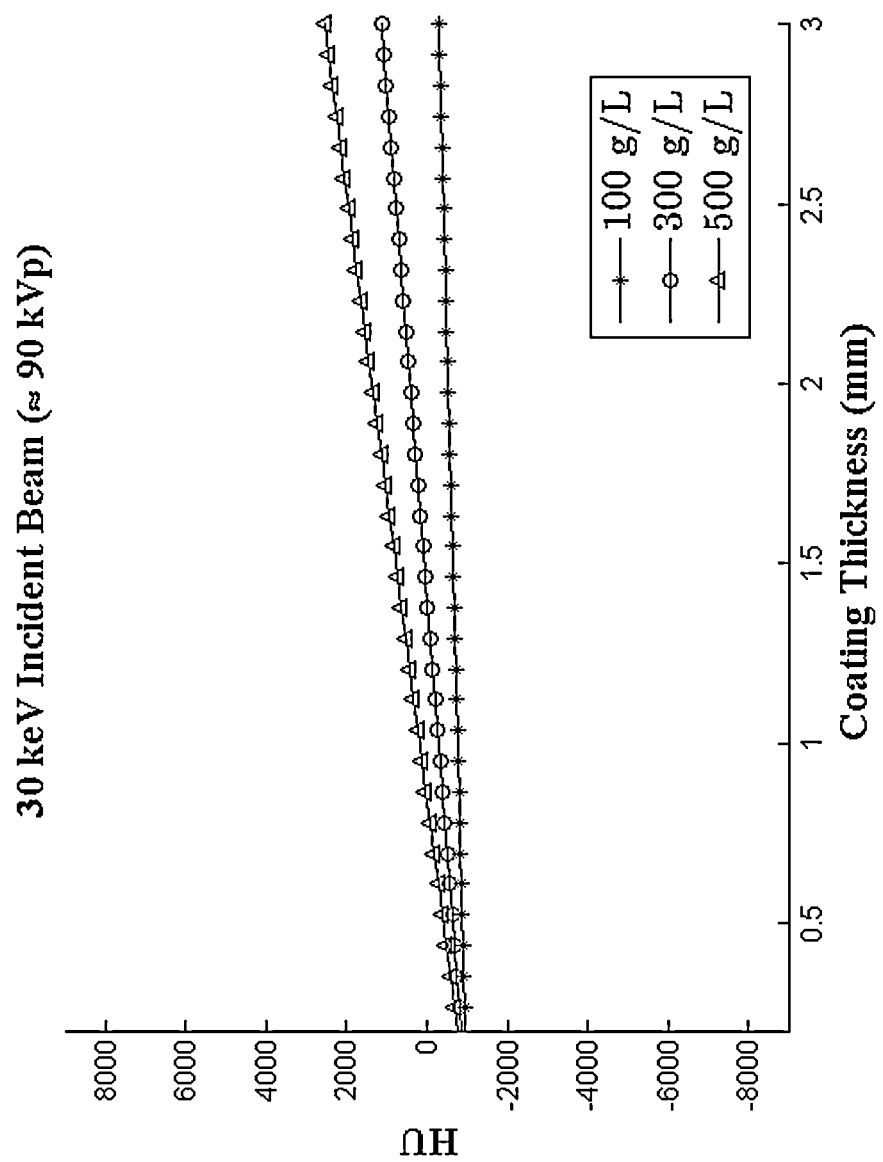
FIG. 19 is a graph showing the theoretical attenuation coefficient (in HU) for various concentrations of bismuth trioxide at varying coating thicknesses for a 30 keV (~90 kVp) incident X-ray beam.
Figure 20:
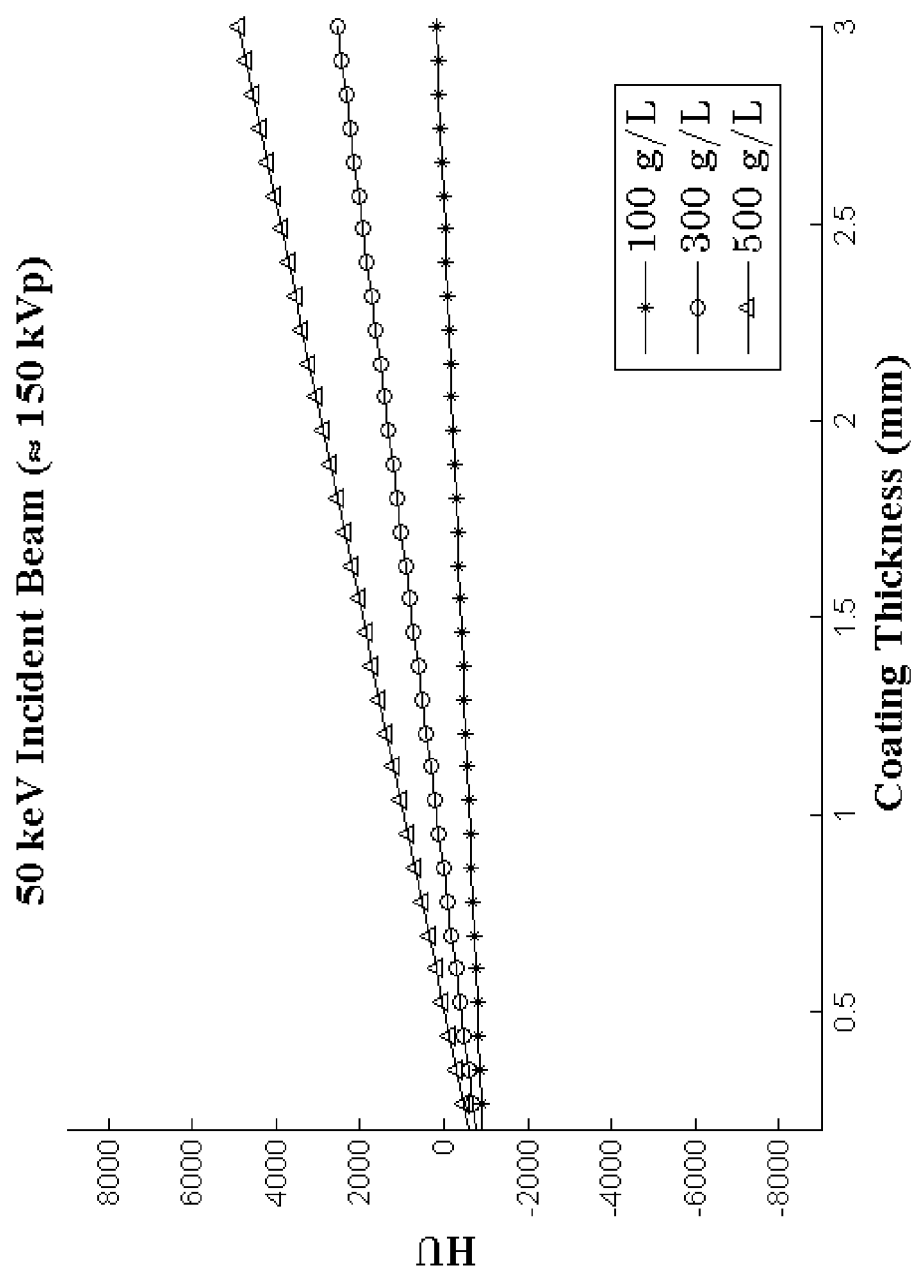
FIG. 20 is a graph showing the theoretical attenuation coefficient (in HU) for various concentrations of bismuth trioxide in inks having varying coating thicknesses for a 50 keV (~150 kVp) incident X-ray beam.
Figure 21:
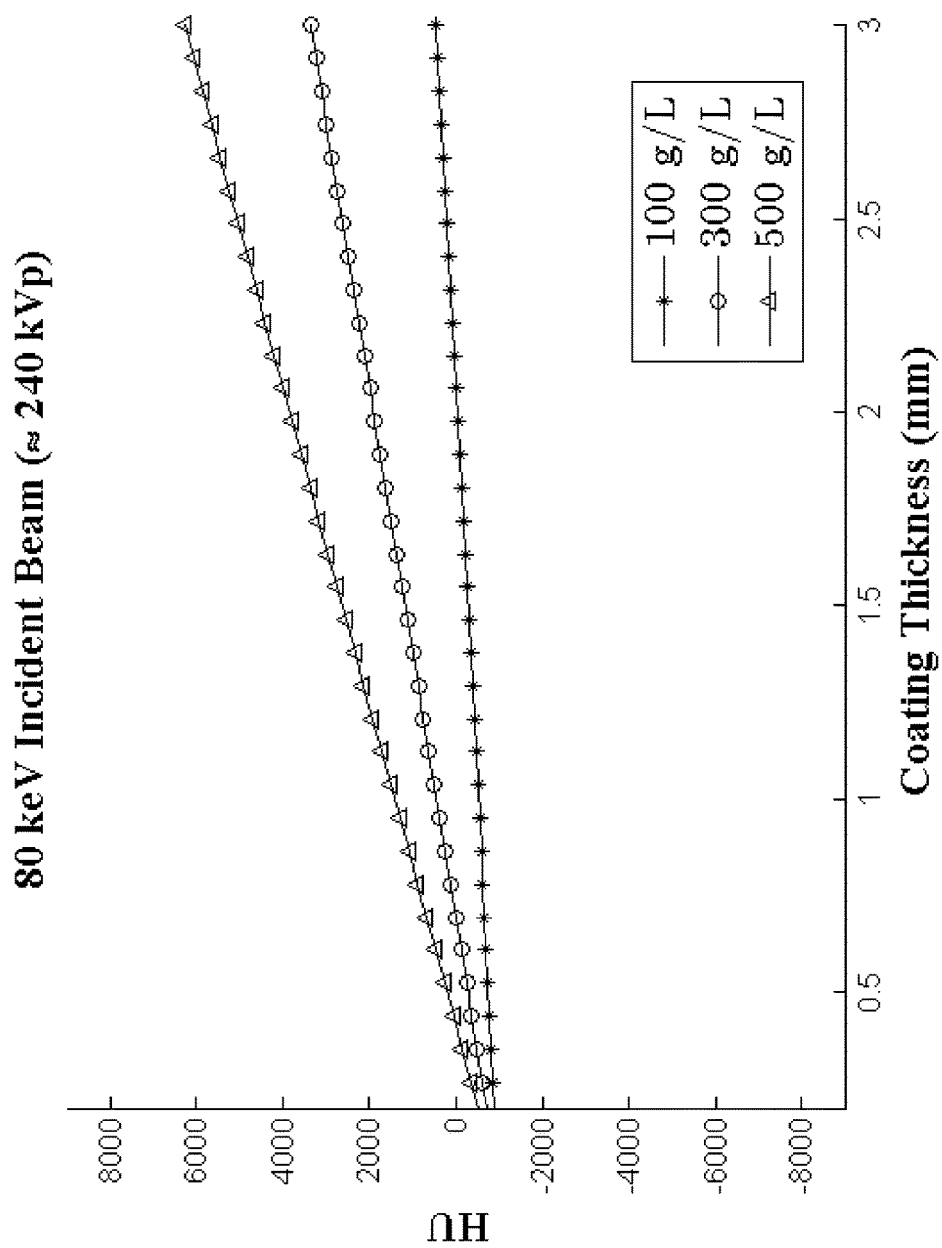
FIG. 21 is a graph showing the theoretical attenuation coefficient (in HU) for various concentrations of bismuth trioxide in inks having varying coating thicknesses for an 80 keV (~240 kVp) incident X-ray beam.

Our choice in using the simple Beer-Lambert equation was designed to answer qualitative questions about which concentrations and coating thicknesses of bismuth (III) oxide would give desired attenuation values of 300-1,000 HU at different incident x-ray energies (FIGS. 19-21). We also used this model to compare attenuation levels (FIG. 22) and attenuation cost efficiency (FIG. 23) at various coating thickness for bismuth (III) oxide against other known radiopaque contrast agents.

As shown in FIGS. 19-21, increasing concentrations of bismuth trioxide are correlated with increased level of attenuation for all clinically relevant incident x-ray energies (90-250 kVp). Increased incident x-ray energy is associated with an decreasing applied layer thickness required to attenuated radiation greater than or equal to water:

TABLE 1

|  | 30 keV | 50 keV | 80 keV |
|---|---|---|---|
| First Coating Thickness Level (500 g/L concentration) Showing Positive Attenuation Relative to Water | 0.8 mm | 0.5 mm | 0.4 mm |

Figure 22:
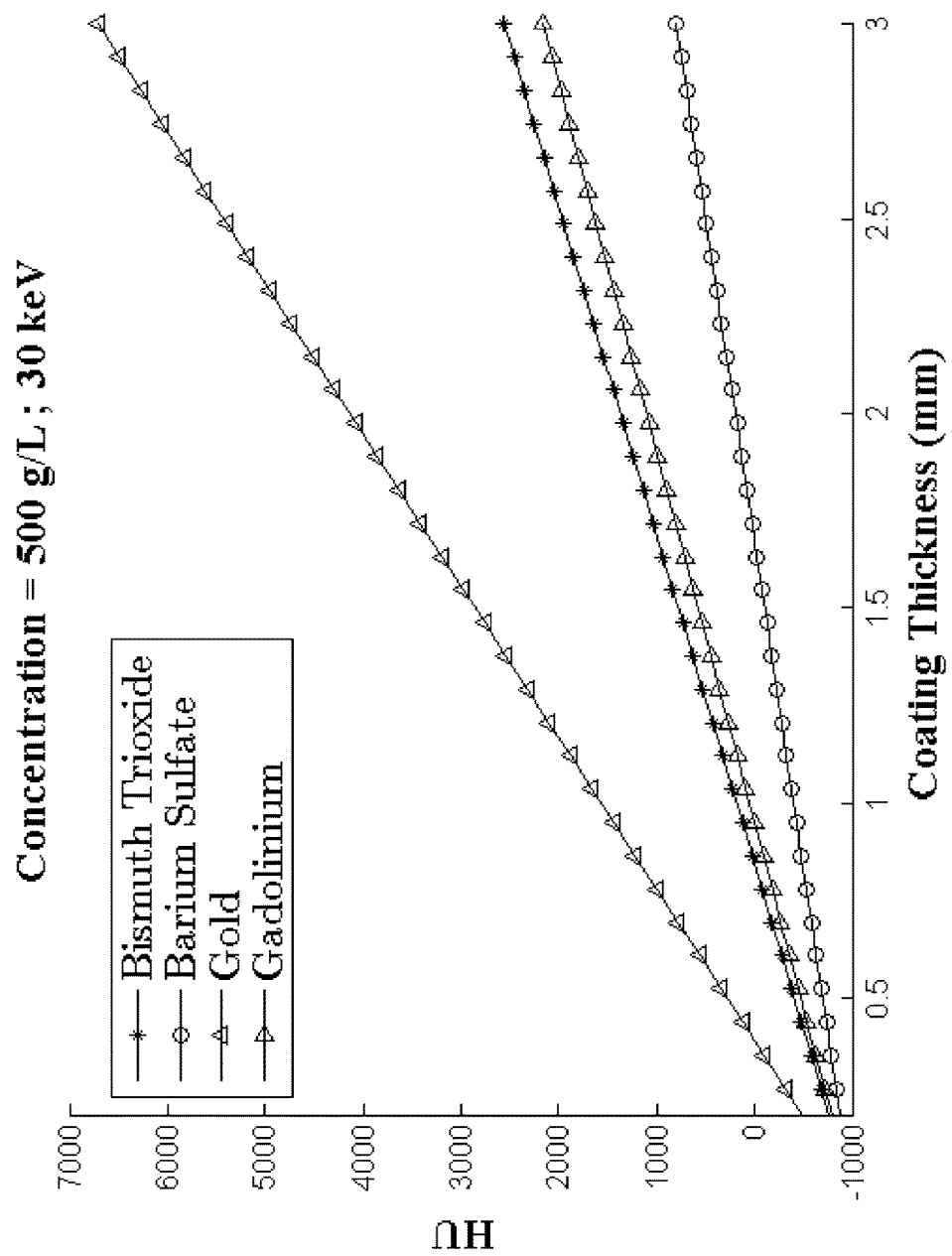
FIG. 22 is a graph showing the theoretical attenuation coefficient (in HU) for various radiopaque particles at concentrations of 500 g/L in inks having varying coating thicknesses for a 30 keV incident X-ray beam.
Figure 23:
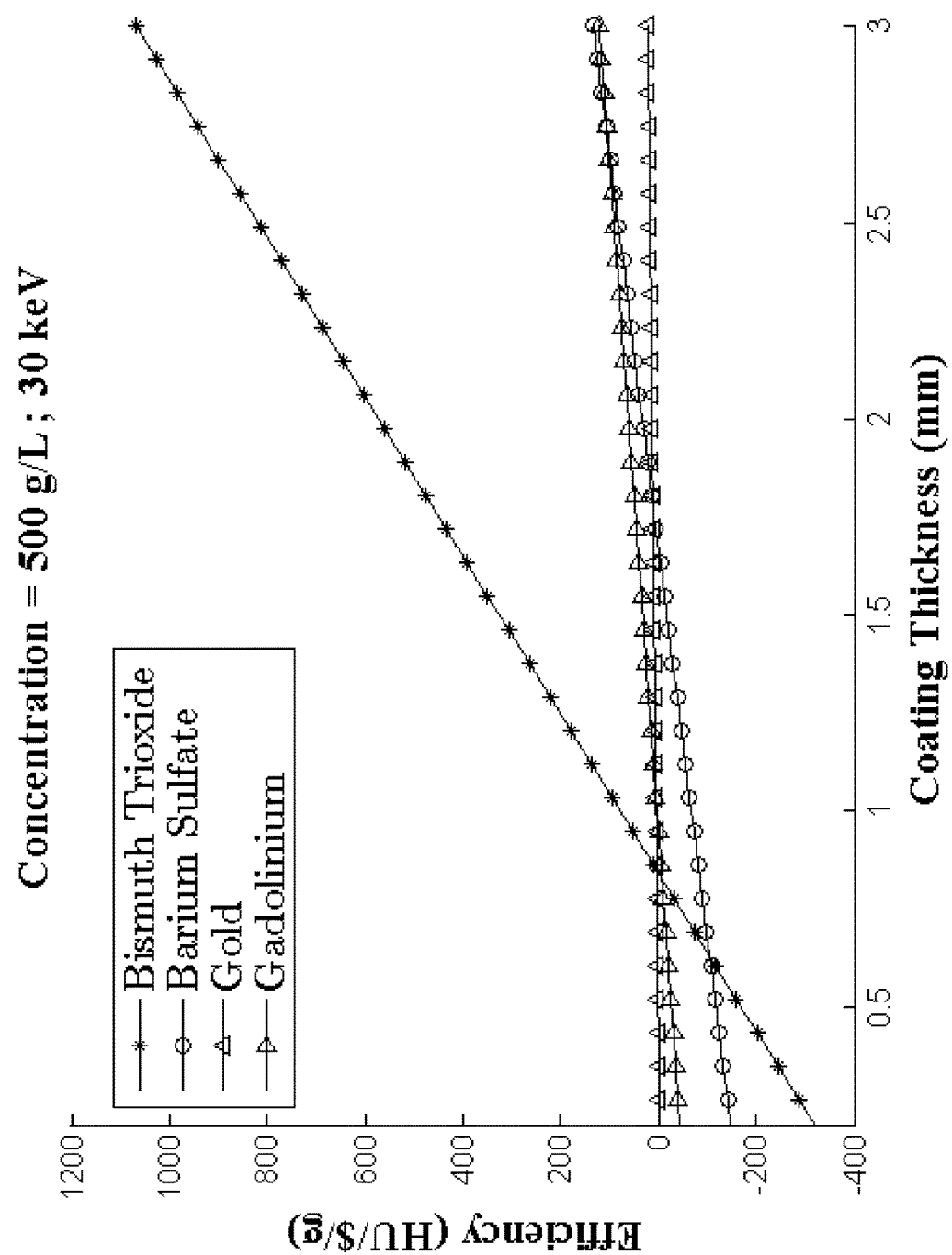
FIG. 23 is a graph showing the theoretical attenuation cost efficiency for various radiopaque substances.

As shown in FIGS. 22 and 23, bismuth trioxide theoretically shows intermediate levels of attenuation relative to water in comparison to other radiopaque contrast agents, but strikes the optimal balance between attenuation at small thicknesses and attenuation cost efficiency.

After predicting the theoretical attenuation coefficients for varying thicknesses of barium trioxide, experiments were conducted to determine the actual attenuation coefficients for barium trioxide. It was experimentally determined that 0.6 mm slices of 500 g/L bismuth trioxide had attenuation coefficients >3,000 HU for, which was substantially greater than what was predicted using the Beer Lambert model. The Siemens software used to measure the attenuation was only calibrated to 3,000 HU, and as such, the 500 g/L bismuth trioxide may be attenuating at much higher levels. This was very unexpected, and may mean that bismuth trioxide may be added to thixotropic solids in low concentrations, and/or applied in very thin layers, to still obtain excellent attenuation. Further experiments will be conducted to confirm this unexpected observation, and to assess the optimal concentrations and application thickness for thixotropic materials containing bismuth trioxide.

REFERENCES

The following references are hereby incorporated by reference in their entireties:

[1] IMV. 2012 Radiographic Fluoroscopy Market Summary Report. 2012. p. IV-1.
[2] CDC. Number of all-listed procedures from discharges from short-stay hospitals by procedure category and age: United States, 2009. 2009.
[3] Pisani L, Lockman D, Jaffray D, Yan D, Martinez A, Wong J. Setup error in radiotherapy: on-line correction using electronic kilovoltage and megavoltage radiographs. International Journal of Radiation Oncology*Biology*Physics. 2000; 47:825-39.
[4] Rathod S, Munshi A, Agarwal J. Skin markings methods and guidelines: A reality in image guidance radiotherapy era. South Asian Journal of Cancer. 2012; 1:27-9.
[5] Probst H, Dodwell D, Gray J C, Holmes M. An evaluation of the accuracy of semi-permanent skin marks for breast cancer irradiation. Radiography. 2006; 12:186-8.
[6] Falahee M. Radiopaque marking pen. Google Patents; 2004.
[7] Zohman G. Implements and methods for applying radiopaque markings. Google Patents; 2008.
[8] Hamilton B H, Hamilton K M. Skin Marking Tool for Radiological Imaging Material. In: Uspto, editor. Charlotte, N.C. 2009.
[9] Sirimanne D L, et al. Subcutaneous Cavity Marking Device. In: Uspto, editor. WI: Devicor Medical Products, Inc.; 2012.
[10] Arnett G W. Radiopaque Landmark Skin Markers and Method. Santa Barbara, Calif.: Arnett Facial Reconstruction Couses, Inc.; 1998.
[11] Cuzner B, Klepak P. Antiperspirants and deodorants. In: Butler H, editor. Poucher's Perfumes, Cosmetics and Soaps: Springer Netherlands; 1993. p. 3-26.
[12] Services USFaDAutUSDoHaH. Summary of Color Additives for Use in the United States in Foods, Drugs, Cosmetics, and Medical Devices. 2013.
[13] Bic Corporation. Round Stic. http://www.bicworld.com/us/products/details/12/round-stic; 2014.
[14] Viscot Medical L. TRADITIONAL INK #1451SR-100. https://www.viscot.com/1451SR-100; 2014.

[15] Shah V. Guidance for Industry: Topical dermatological drug product NDAs and ANDAs-In vivo bioavailability, bioequivalence, in vitro release, and associated studies. 1998.
[16] Bushberg J T. The Essential Physics of Medical Imaging: Lippincott Williams & Wilkins; 2002.
[17] Mathieu K B, Kappadath S C, White R A, Atkinson E N, Cody D D. An empirical model of diagnostic x-ray attenuation under narrow-beam geometry. Medical Physics. 2011; 38:4546-55.
[18] Seltzer S M, Hubbell J H. Tables and Graphs of Photon Mass Attenuation Coefficient and Mass Energy-Absorption Coefficients for Photon Energies 1 keV to 20 MeV for Elements Z=1 to 92 and Some Dosimetric Materials, Appendix to invited plenary lecture by J. H. Hubbell "45 Years (1950-1995) with X-Ray Interactions and Application. 51st National Meeting of the Japanese Society of Radiological Technology. Nagoya, Japan 1995.
[19] http://www.augmenix.com/products/traceit/
[20] http://www.cimedical.com/Inks/radiopaque-ink.html
[21] http://www.bardbiopsy.com/products/index_markers.php
[22] http://www.radiopaque1.com/home.html
[23] http://www.terumois.com/products/sheaths/destination.aspx
[24] http://www.carbo-fix.com/Products/CarboFixNails/Radiopaquemarkers.aspx
[25] http://www.universalmedicalinc.com/Lead-Markers-s/314.htm
[26] http://www.izimed.com/whats_new.shtml
[27] http://www.suremark.com/catalog/
[28] U.S. Patent Application Publication No. 2004/0127824.
[29] U.S. Patent Application Publication No. 2008/0009718.
[30] U.S. Patent Application Publication No. 2009/0253981.
[31] U.S. Pat. No. 5,848,125.
[32] U.S. Pat. No. 8,320,993.

What is claimed is:

1. A marking implement for making a radiopaque marking, comprising a marking element formed of a composition comprising a carrier and a plurality of bismuth trioxide particles dispersed in the carrier, wherein the composition:
is a thixotropic solid that maintains its shape at ambient temperatures but is deposited on skin at thicknesses between about 0.1 mm and about 1.5 mm when a shear force of between about 10N to about 35N is applied between the composition and the skin; and
has an attenuation coefficient of greater than about 1,000 Hounsfield units (HU) at a thickness of about 0.6 mm for an x-ray having an incident intensity of about 135 kVp and about 1.5 mA.

2. The marking implement of claim 1, wherein the bismuth trioxide particles have average diameters between about 90 nm and about 210 nm.

3. The marking implement of claim 1, wherein the concentration of bismuth trioxide in the composition is between about 50 g/L and about 750 g/L.

4. The marking implement of claim 1, wherein the concentration of bismuth trioxide in the composition is between about 100 g/L and about 600 g/L.

5. The marking implement of claim 1, wherein the concentration of bismuth trioxide in the composition is between about 300 g/L and about 550 g/L.

6. The marking implement of claim 1, wherein the carrier comprises propylene glycol, dipropylene glycol and sodium stearate.

7. The marking implement of claim 6, wherein the carrier comprises:
about 35 wt % to about 50 wt % propylene glycol;
about 10 wt % to about 15 wt % dipropylene glycol; and
about 2 wt % to about 15 wt % sodium stearate.

8. The marking implement of claim 6, wherein the carrier further comprises one or more of fumed silica and cyclomethicon.

9. The marking implement of claim 8, wherein the carrier comprises:
about 10 wt % to about 15 wt % fumed silica; and
about 5 wt % to about 10 wt % cyclomethicone.

10. The marking implement of claim 1, wherein the composition further comprises a coloring agent.

11. The marking implement of claim 10, wherein the coloring agent comprises erioglaucine disodium salt.

12. The marking implement of claim 1, wherein the composition has an attenuation coefficient of greater than about 2,000 HU at a thickness of about 0.6 mm for an X-ray having an incident intensity of about 135 kVp and about 1.5 mA.

13. The marking implement of claim 1, wherein the composition has an attenuation coefficient of greater than about 3,000 HU at a thickness of about 0.6 mm for an X-ray having an incident intensity of about 135 kVp and about 1.5 mA.

14. The marking implement of claim 1, wherein the composition is washable in water so as not to be visible to the naked eye.

15. A marking implement for making a radiopaque marking, comprising a marking element formed of a composition comprising a carrier and a plurality of bismuth trioxide particles dispersed in the carrier, where the carrier is a thixotropic solid that maintains its shape at ambient temperatures but is deposited on skin at thicknesses between about 0.1 mm and about 1.5 mm when a shear force of between about 10N to about 25N is applied between the composition and the skin, and comprises comprising:
about 35 wt % to about 50 wt % propylene glycol;
about 10 wt % to about 15 wt % dipropylene glycol; and
about 2 wt % to about 15 wt % sodium stearate.

16. The marking implement of claim 15, wherein the bismuth trioxide particles have average diameters between about 90 nm and about 210 nm.

17. The marking implement of claim 15, wherein the concentration of bismuth trioxide in the composition is between about 50 g/L and about 750 g/L.

18. The marking implement of claim 15, wherein the concentration of bismuth trioxide in the composition is between about 100 g/L and about 600 g/L.

19. The marking implement of claim 15, wherein the concentration of bismuth trioxide in the composition is between about 300 g/L and about 550 g/L.

20. The marking implement of claim 15, wherein the carrier further comprises one or more of fumed silica and cyclomethicone.

21. The marking implement of claim 20, wherein the carrier comprises:
about 10 wt % to about 15 wt % fumed silica; and
about 5 wt % to about 10 wt % cyclomethicone.

22. The marking implement of claim 15, wherein the composition further comprises a coloring agent.

23. The marking implement of claim 22, wherein the coloring agent comprises erioglaucine disodium salt.

24. The marking implement of claim 15, wherein the composition is washable in water so as not to be visible to the naked eye.

25. A method of facilitating a surgical procedure, comprising:

locating a position on the skin of a patient relative to a target surgical site;

marking the position on the skin using the implement of claim 1; and subjecting the target surgical site and the marked location to x-ray exposure to view the target surgical site and the mark under x-ray.

\* \* \* \* \*